United States Patent
King

(10) Patent No.: US 7,546,164 B2
(45) Date of Patent: **\*Jun. 9, 2009**

(54) ELECTRICAL TISSUE STIMULATION APPARATUS AND METHOD

(75) Inventor: Gary William King, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 750 days.

This patent is subject to a terminal disclaimer.

(21) Appl. No.: 10/805,028

(22) Filed: Mar. 19, 2004

(65) Prior Publication Data

US 2004/0186544 A1 Sep. 23, 2004

Related U.S. Application Data

(63) Continuation of application No. 10/007,508, filed on Nov. 7, 2001, now Pat. No. 6,745,079.

(51) Int. Cl.
*A61N 1/00* (2006.01)
(52) U.S. Cl. .......................................... 607/117; 607/46
(58) Field of Classification Search ................. 607/115, 607/122, 116, 117, 46, 43
See application file for complete search history.

(56) References Cited

U.S. PATENT DOCUMENTS

| | | | |
|---|---|---|---|
| 3,737,579 A | 6/1973 | Bolduc | |
| 3,974,834 A | 8/1976 | Kane | |
| 4,209,019 A | 6/1980 | Dutcher et al. | |
| 4,217,913 A | 8/1980 | Dutcher | |
| 4,285,347 A * | 8/1981 | Hess | 607/117 |
| 4,301,815 A | 11/1981 | Doring | |
| 4,311,153 A | 1/1982 | Smits | |
| 4,323,081 A | 4/1982 | Wiebusch | |
| 4,394,866 A | 7/1983 | Hughes | |
| 4,414,986 A | 11/1983 | Dickhudt et al. | |
| 4,419,819 A | 12/1983 | Dickhudt et al. | |
| 4,465,079 A | 8/1984 | Dickhudt | |
| 4,498,482 A | 2/1985 | Williams | |

(Continued)

FOREIGN PATENT DOCUMENTS

CA          2361777          5/2002

(Continued)

OTHER PUBLICATIONS

Research Disclosure, "Shape-Memory Neurological Lead", Disclosed anonymously 35311, 1 pg. (Sep. 1993), Author unknown..

(Continued)

*Primary Examiner*—Scott M Getzow
(74) *Attorney, Agent, or Firm*—John W. Albrecht; Stephen W. Bauer

(57) ABSTRACT

An implantable lead for electrical stimulation of tissue has wire-like extendable members whose tips curl back upon themselves in open tissue spaces to form 2- or 3-dimensional electrodes. The electrodes may be positioned axially or in other directions from the lead body. Traction on the lead body or extendable members allows easy withdrawal as the member tip electrodes uncurl, allowing removal without major surgery. This apparatus and method is useful for minimally invasive insertion of electrodes or electrode arrays, especially through a narrow body lumen or Tuohy needle, providing therapeutic stimulation of nervous tissue, muscle or organs.

25 Claims, 14 Drawing Sheets

U.S. PATENT DOCUMENTS

| | | | |
|---|---|---|---|
| 4,590,949 A | 5/1986 | Pohndorf | |
| 4,628,944 A | 12/1986 | MacGregor et al. | |
| 4,686,765 A | 8/1987 | Byers et al. | |
| 4,699,147 A | 10/1987 | Chilson et al. | |
| H356 H | 11/1987 | Stokes et al. | |
| 4,716,888 A | 1/1988 | Wesner | |
| 4,722,353 A | 2/1988 | Sluetz | |
| 4,796,643 A | 1/1989 | Nakazawa et al. | |
| 4,945,922 A | 8/1990 | van Krieken | |
| 4,971,070 A | 11/1990 | Holleman et al. | |
| 5,052,407 A | 10/1991 | Hauser et al. | |
| 5,105,826 A | 4/1992 | Smits et al. | |
| 5,121,754 A | 6/1992 | Mullett | |
| 5,127,421 A | 7/1992 | Bush et al. | |
| 5,179,962 A | 1/1993 | Dutcher et al. | |
| 5,215,089 A | 6/1993 | Baker, Jr. | |
| 5,259,394 A | 11/1993 | Bens | |
| 5,282,845 A | 2/1994 | Bush et al. | |
| 5,300,107 A | 4/1994 | Stokes et al. | |
| 5,314,462 A | 5/1994 | Heil, Jr. et al. | |
| 5,344,439 A | 9/1994 | Otten | |
| 5,350,419 A | 9/1994 | Bendel et al. | |
| 5,397,343 A | 3/1995 | Smits | |
| 5,405,374 A | 4/1995 | Stein | |
| 5,425,756 A | 6/1995 | Heil, Jr. et al. | |
| 5,462,545 A * | 10/1995 | Wang et al. | 606/41 |
| 5,476,498 A | 12/1995 | Ayers | |
| 5,514,174 A | 5/1996 | Heil, Jr. et al. | |
| 5,531,783 A * | 7/1996 | Giele et al. | 607/126 |
| 5,545,207 A | 8/1996 | Smits et al. | |
| 5,628,778 A | 5/1997 | Kruse et al. | |
| 5,716,391 A | 2/1998 | Grandjean | |
| 5,807,399 A | 9/1998 | Laske et al. | |
| 5,837,006 A | 11/1998 | Ocel et al. | |
| 5,846,196 A | 12/1998 | Siekmeyer et al. | |
| 5,871,530 A | 2/1999 | Williams et al. | |
| 5,897,585 A | 4/1999 | Williams | |
| 5,919,222 A | 7/1999 | Hjelle et al. | |
| 5,999,858 A | 12/1999 | Sommer et al. | |
| 6,006,122 A | 12/1999 | Smits | |
| 6,038,472 A | 3/2000 | Williams et al. | |
| 6,055,457 A | 4/2000 | Bonner | |
| 6,093,197 A | 7/2000 | Bakula et al. | |
| 6,094,596 A | 7/2000 | Morgan | |
| 6,108,582 A | 8/2000 | Fischer, Sr. | |
| H1905 H | 10/2000 | Hill | |
| 6,132,456 A | 10/2000 | Sommer et al. | |
| 6,133,547 A | 10/2000 | Maynard | |
| 6,161,047 A | 12/2000 | King et al. | |
| 6,169,269 B1 | 1/2001 | Maynard | |
| 6,178,355 B1 | 1/2001 | Williams et al. | |
| 6,240,322 B1 | 5/2001 | Peterfeso et al. | |
| 6,697,677 B2 * | 2/2004 | Dahl et al. | 607/128 |
| 2001/0005783 A1 * | 6/2001 | Hassett | 604/523 |

FOREIGN PATENT DOCUMENTS

| | | |
|---|---|---|
| EP | 0479435 A2 | 4/1992 |
| EP | 0965359 A2 | 12/1999 |
| WO | WO 98/48887 A1 | 11/1998 |

OTHER PUBLICATIONS

Canadian Office Action, Issued Jan. 5, 2009.

* cited by examiner

ELECTRICAL TISSUE STIMULATION APPARATUS AND METHOD

RELATED APPLICATION

This application is a continuation of U.S. patent application Ser. No. 10/007,508, filed Nov. 7, 2001, which is hereby incorporated herein by reference in its entirety.

FIELD OF THE INVENTION

This invention relates generally to medical devices, and more particularly to particularly to an implantable lead.

BACKGROUND OF THE INVENTION

For more than 30 years, electrical stimulation of nervous tissue has been used to control chronic pain. Therapy originates from an implanted source device, called an electric signal generator. The electrical signals, usually a series of brief duration electrical pulses, are delivered through one or more implanted leads that communicate with the source device, and contain several conductive metal electrodes to act as low impedance pathways for current to pass to tissues of interest. For example, in spinal cord stimulation (SCS) techniques, electrical stimulation is provided to precise parts of the human spinal cord through a lead that is usually deployed in the epidural space dorsal to the spinal cord. Such techniques have proven effective in treating or managing disease and chronic pain conditions.

Percutaneous leads are small diameter leads that may be inserted into the human body through a Tuohy (non-coring) needle, which includes a central lumen through which the lead is guided. Percutaneous leads are advantageous because they may be inserted into the body with a minimum of trauma to surrounding tissue. On the other hand, the designs of lead structure that may be incorporated into percutaneous leads are limited because the lead diameter or cross-section must be small enough to permit the lead to pass through the Tuohy needle, generally less than 2.0 mm diameter. Typically, the electrodes, also called contacts, on percutaneous leads are cylindrical metal structures, with a diameter of approximately 1.0 mm and a length of 4.0 to 10.0 mm. Of course, half of each of these electrodes, facing away from the tissue of interest, is not very useful in delivering therapeutic current. Thus the surface area of electrodes that face the tissue to be excited is small, typically 3.0 to 10.0 square mm. Electrodes must be approximately this size for many human applications, especially SCS, to allow sufficient charge to be delivered with each electrical pulse to excite cells, but without a high charge density (charge/pulse/square mm) that might damage tissue or the electrode itself.

Paddle leads, like Model 3596 Resume® Lead, Model 3982 SymMix® Lead or Model 3991 Transverse Tripole® Lead of Medtronic, Inc., have been developed to offer improved therapy control over some aspects of percutaneous leads. Paddle leads include a generally two-dimensional array of electrodes on one side of an insulative body, for providing electrical stimulation to excitable tissue of the body. A paddle design allows electrodes to be considerably wider than percutaneous leads, up to 4.0 mm or more. Two-dimensional arrays of electrodes allow programming of active sites and better control of the electric field distribution.

One disadvantage recognized in known paddle leads is that their installation, repositioning and removal necessitates laminectomy, which is a major back surgery done by neurosurgeons and orthopedic surgeons, involving removal of part of the vertebral bone. Laminectomy is required because paddle leads have a relatively large width (up to 1.0 cm or more) compared to percutaneous leads. Thus, implantation, repositioning or removal of a paddle lead requires a rather large opening between the vertebral bones.

Electrodes on paddle leads can easily have larger surface areas than percutaneous leads, typically 8.0 to 20.0 square mm or more. Such electrodes are mainly circular or rectangular, and require welds to fine, flexible wires passing through the length of the lead body. Such welds are prone to breakage in high flex situations unless a relatively thick paddle is used to shield the welds and support the electrodes. One advantage of preferred embodiments of the invention is that welds are not required in places where they might encounter flexing.

Because of the size and relative stiffness of paddle leads compared to the tissues they lie near to, more scar tissue or fibrosis tends to form around them over time than around percutaneous leads. This can reduce electrical efficiency, and lead to the need for larger currents over time. Such scar tissue also necessitates greater surgical efforts for removal of paddle leads, if required. On some occasions, physicians have even clipped off the lead body and left a paddle permanently in a patient rather that surgically remove it, if the system should cease giving therapeutic benefit.

For these above listed benefits and liabilities, there is a need for a lead that can be percutaneously inserted through a Tuohy-type needle, but which can create electrodes, each with substantial 2-dimensional surface area, at positions that are more lateral than the current percutaneous lead bodies. Furthermore, if such a lead could be safely removed by simple traction on the lead body, the increased surgical efforts that are required of paddle-type leads could be avoided.

The prior art has shown some examples of leads that can be expanded in situ, but they cannot perform all of the above listed features.

Mullett in U.S. Pat. No. 5,121,754 described a percutaneously-inserted epidural stimulation lead that can be straightened by a stylet and inserted into the epidural space through a Tuohy needle, and then will assume a sigmoidal shape that had been preset in it once the stylet is removed. This allows a plurality of electrodes to be positioned at a variety of longitudinal and lateral positions over the dorsal surface of the spinal cord. Because each electrode is a cylindrical metal electrode of fixed size and shape, the device cannot reliably place several electrodes at each longitudinal position. With a diameter less than 2.0 mm, each electrode must have a length of several millimeters to pass adequate currents for SCS (typically 10-20 milliamperes). Hence on such simple percutaneous leads the electrodes are manufactured as metal cylinders whose diameter matches the lead diameter. In addition, there is a problem with getting the various electrodes into lateral positions: once the stylet is removed, the preset sigmoidal shape returns, but only until the lateral forces generated by the preset curves equal the strength of various unpredictable adhesions between the dura and the vertebral bones or ligamentum flavum to resist the forces. In practice, since such leads are near the delicate spinal cord and flexible dura, they must have a high degree of flexibility once the straightening stylet is removed, and this may prevent achievement of the degree of lateral electrode positioning that is desired.

Conducting coils have been used in at least parts of leads to assist defibrillation of the heart (Smits & Camps, U.S. Pat. No. 5,105,826; Holleman, Sandstrom, Rugland & Williams, U.S. Pat. No. 4,971,070). While these have a degree of flexibility and even sigmoidal or spiraling shapes, they were designed to not change their shape, nor will they pass through a Tuohy needle lumen of 2.0 mm or less. Another conducting coil was built to have two or more alternating, generally coplanar curves to act as a defibrillation device inside the heart (Stein, U.S. Pat. No. 5,405,374). However, this has a very large curving electrode, spanning an area of approximately 40 mm×40 mm, designed to touch the heart tissue at two or three places, and does not curl back upon itself in a spiral manner. Cardiac leads often have preset curves to enable the electrodes to contact specific tissue inside the heart (Kruse, Lokhoff and van Venrooij, U.S. Pat. No. 5,628,778; Hughes, U.S. Pat. No. 4,394,866). One design had a "resiliently coiled configuration", with two 360-degree turns (Ayers, U.S. Pat. No. 5,476,498), but the curving parts are insulated, several centimeters in diameter, and used for fixation of the lead inside the heart chambers.

A shape-memory neurological lead for use in the epidural space was described in WPI Acc No: 93-342955/199343. The lead as finger-shaped wings made from shape-programmable, thermal sensitive metal and/or polymer, e.g., a bimetal or nitinol alloy. At room temperature, the wings will lay along side the lead body, which can be inserted through a needle to be positioned in the epidural space. Once implanted, at body temperature the wings will move outward into their pre-programmed shape, expanding each on in one direction, to fixate the lead optimally with respect to the boundaries of the epidural space. However, there are no conducting electrodes on the tips of the stabilization wings, and the motion is more like a person raising their arms out from the body, and not, like a person with outstretched arms curling up their fingers to form fists.

Siekmeyer and van Erp (U.S. Pat. No. 5,846,196) describe a temporary multielectrode cardiac mapping probe. The probe is believed to likely have a larger diameter than will fit through the lumen of an epidural Tuohy needle (about 2.0 mm maximum). In one embodiment, two member wires are advanced out of a confining sheath inside a heart chamber, and due to their preset elastic curves, expand to stretch out a sheet array of many recording electrodes that was folded or rolled into a compact shape inside the sheath. The electrodes are each of a fixed 2-dimensional size and rectangular shape. Since the device was not intended to be permanently implanted in the human body, the advanced members are withdrawn back into the sheath after the mapping or ablation procedure is done, collapsing by rolling or folding the sheet of electrodes again to fit in the narrow width sheath. The device has the ability to carry electrodes to more lateral positions than the width of the sheath. However, the sheath must be wide enough to accommodate the widths of numerous hard, metal electrodes when the sheet of them is made compact again. If those electrodes were of the size required for tissues stimulation, and not recording electrodes, the sheath would be 10 mm in diameter or larger. The planar sheet of electrodes may have a backing of shape memory material, perhaps made of nitinol, which also can change its conformational shape due to change in temperature inside versus outside the body, or by means of heating elements.

Chilson and Smith (U.S. Pat. No. 4,699,147) also described a cardiac mapping device that had four wires each with multiple recording electrodes, that will move apart in their middle region once they are deployed out of a sheath, forming a 3-dimensional surface, but it is similar to the device in the '196 patent, and will not perform any better for chronic tissue stimulation.

However, an optimal permanently implantable lead for tissue stimulation must have several additional features for use in the human body. It must allow the placement and use of substantially large conducting electrodes that are needed to safely and reliably pass stimulation electrical pulses of adequate amplitudes to excite tissue cells over indefinitely long periods of time, typically each about 2.0×4.0 mm or larger. To greatly minimize surgical trauma during implantation, the lead should be able to have the electrodes assume a 1-dimensional shape that is very narrow (less than 0.5 mm) inside the lead body (or sheath) for passage through a small catheter or Tuohy needle, and to assume a 2-dimensional shape when outside the lead body. Since there may be considerable deposits of fibrosis or scar tissue around each electrode within a few months of permanent implantation, if necessary, the lead should be able to be removed by gentle traction on the lead body, and have all parts easily disengage from the tissue, again without major surgical trauma.

King, Rise, Schendel and Schallhorn (U.S. Pat. No. 6,161,047) described seven lead designs that are compact and can be inserted through a sheath or Tuohy needle, and can be expanded in situ or even collapsed and removed through the lead body or sheath. Some of these use preset elastic materials to help the lead expand once it is in a position where expansion is safe, i.e., in a tissue space in the body. However, in each instance the conducting electrodes are metallic with a permanent, sizeable 2-dimensional surface at all times.

Furthermore, many of the current designs of implanted epidural stimulation leads do not have sufficient flexibility to function well in areas of great mechanical movement. For example, epidural stimulation leads in the cervical spinal cord are under great movement due to flexing of the neck. Percutaneous leads, and even paddle leads, can deliver paresthesia (the tingling feeling of stimulation that is necessary for pain relief). However, with currently available models, after implant the paresthesia may vary from nonexistent to very painful (too intense) during modest movements of the head. This is most frustrating to the patient, and prevents use of stimulation during sleep, when it may be most needed. Practitioners have gone to great lengths, and extensive surgery, to suture small paddles to the dura mater for cervical applications. An implantable lead with an array of electrodes that is very flexible and that even can urge each electrode toward the dura mater independently would be a very useful for epidural stimulation in the cervical region.

Finally, the dura mater is curved. Paddle leads generally are flat, so it is possible that several of their electrodes might not be touching the dura mater at all times. If some of them should be several millimeters away from the dura mater, scar tissue or even the fat cells that are found in the epidural space might become lodged between the dura mater and the electrodes, greatly diminishing the efficiency of the stimulation due to higher impedance for current that might otherwise pass into the spinal cord.

SUMMARY OF THE INVENTION

This invention relates to implantable leads for delivering electrical stimulation to tissue in the human body. Specifically, this invention relates to implantable leads that have thin, wire-like, moveable elongate members that may be elastically deformed, but with a distal tip that can curl up in a space inside the body to form a 2- or 3-dimensional electrode for delivery of electrical pulses. Members can be positioned axially or at variable non-axial distances from the lead body. This invention also relates to mechanisms for accomplishing the insertion of multiple electrodes in a manner that is minimally invasive, even through a narrow lumen like a vertebral foramen. An array of such electrodes can also be easily removed without major surgical intervention.

Preferred embodiments of the invention combine the advantages of percutaneous leads with those of paddle leads, both of which are permanently implanted in the human body for electrical stimulation of excitable tissue. In a preferred embodiment, a lead body is provided that can be passed through a Tuohy needle and which can spread over several dimensions an array of 2-dimensional electrodes. These electrodes are located on the tips of moveable, extendable members, which, once deployed beyond the confines of the lead body, will curl up into 2-dimensional electrodes. If the lead should need to be removed, the lead body or its extendable members can be retracted, and the electrodes will uncurl and become straight as they are drawn back into the lead body. This can be done without major surgical intervention.

The part of an extendable member that curls into a 2-dimensional conductive pad or 3-dimensional electrode is composed of a robust and safe material, such as platinum or platinum/iridium. Those metals, or a composite of similar metals over a substrate, are treated by heat, pressure or chemicals so that they have a preset tendency to curl up, especially when it is no longer confined in a channel of the lead body. The tip that curls may be a coiled conductor, much like a spring.

In an embodiment, the curling part of an extendable member may have a bimetallic nature so it will curl at a given temperature, or it may be made of nitinol or other hyperelastic materials, that may require heating to certain temperatures to effect shape changes.

Regarding the positioning of electrodes, in a preferred embodiment, each extendable member can be positioned independently, or groups of them can be moved in unison. Each member has a portion that may have a preset curve to allow the tip of that member, with its curled electrode, to be positioned more laterally or more ventrally (toward the dura matter for epidural stimulation) than the tip of the lead body itself. Each member may have an asymmetry to match an asymmetry in its channel, so that its deployment is in a fixed direction from the lead body. Alternatively, the implanting physician may be able to use fluoroscopy to send each member's tip in any preferred direction.

By having a curve to allow deployment of the extendable member's tip non-axially, various degrees of non-axial placement of a electrode can be controlled by the length of deployment of the extendable member outside of the lead body. The member in this case needs an elastic ability to be straightened (when so confined) or to curve (when no longer confined).

For epidural SCS, if there is a curve in the extendable member to allow deployment of the member's tip ventrally (toward to the spinal cord), each member may be positioned to allow it's curled top to lie against the curved surface of the dura matter. Thus, an array of such electrodes can match the curvature of the dura mater, and keep a more constant distance from the spinal cord.

In an embodiment, the extendable member may be composed of a coiled conductor to have great flexibility. This design would use an internal wire spanning at least some portions to give the member sufficient curvature to allow its deployment from the lead body in specific directions. There would be insulation on the outside except at the proximal end, which is electrically connected to the pulse source, and at the distal end, which curls into a conducting electrode. There might also be two or more coiled conductors, dissimilar in properties, which are bonded, hooked or welded to the tip of the member.

In another embodiment, a coiled conductor may be found only at the distal end of the extendable member, with most of the length of the member being a simple metal wire, insulated to prevent current loss except at the conducting tip. This coiled conductor may screw on to the end of the wire.

In order to prevent curling of the electrode before the end of the extendable member is in its final position, the tip of the member may be coated with a material that keeps it rigidly straight. This material would dissolve over time in the environment of the body, allowing curling of the tip into an electrode. The material may also have a sharp point, to make the deployment of the member through adhesions or other tissue easier.

In a further embodiment, the lead may be designed to allow placement of sizeable 2- or 3-dimensional electrodes through a very small lumen in the body, such as a vertebral or sacral foramen, for peripheral nerve stimulation. This can be done with a smaller diameter lead body than other currently available lead designs, which have rigid electrodes.

Other advantages, novel features, and further scope of applicability of the present invention will be set forth in the detailed description to follow, taken in conjunction with the accompanying drawings, and in part will become apparent to those skilled in the art upon examination of the following, or may be learned by practice of the invention. For example, although the examples herein depict electrical electrodes that are essentially 2-dimensional, a 3-dimensional ball electrode may also be assembled by curling of the tip of an extendable member that has been appropriately preset by treatments.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings, in which like numbers refer to like parts throughout.

DESCRIPTION OF PREFERRED EMBODIMENTS

Figure 1:
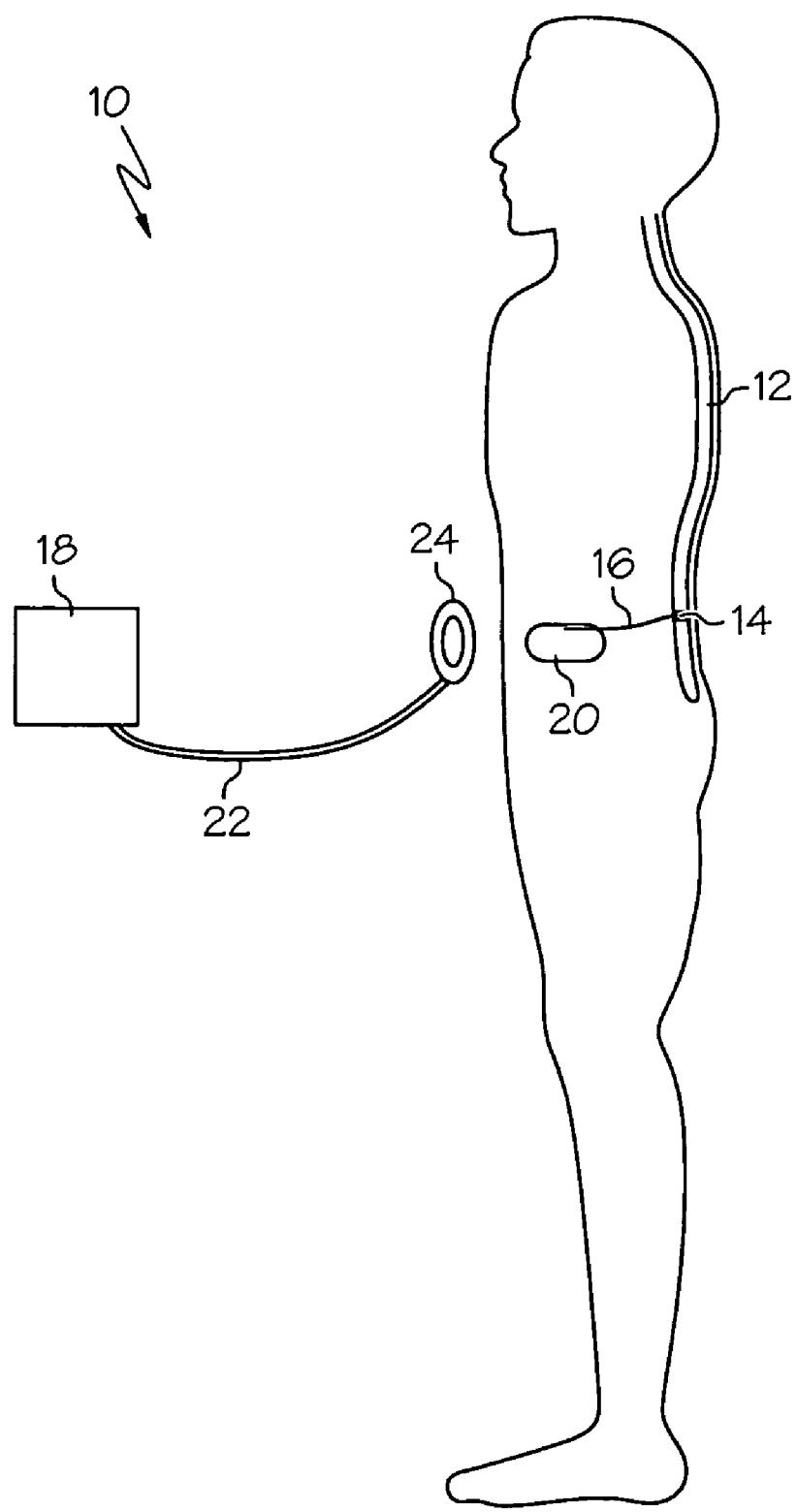
FIG. 1 is a schematic view of a patient with a chronically implanted neurological stimulation system employing a preferred embodiment of the invention.

FIG. 1 is a schematic view of patient 10 having an implant of a neurological stimulation system employing an embodiment of the invention. The preferred system uses a programmer 18 that is coupled via conductor 22 to radio-frequency antenna 24. This permits attending medical personnel to change various stimulation parameters after implant using the radio-frequency communication.

This communication is directed to an implantable pulse generator 20. The stimulation pulses are produced by implantable pulse generator 20, which is preferably an Itrel II® or Synergy® implantable neurological pulse generator available from Medtronic, Inc.

The stimulation pulses produced by implantable pulse generator 20 are coupled to spinal cord 12 using insulated lead 16, sometimes using also a connecting segment called an extension (not shown). The electrodes of insulated lead 16 are located at its distal end 14 located near the spinal cord 12.

Though the preferred mode employs fully implanted elements, systems employing partially implanted generators and radio-frequency coupling from an external battery may also be used with leads of alternative embodiments of the invention.

Figure 2:
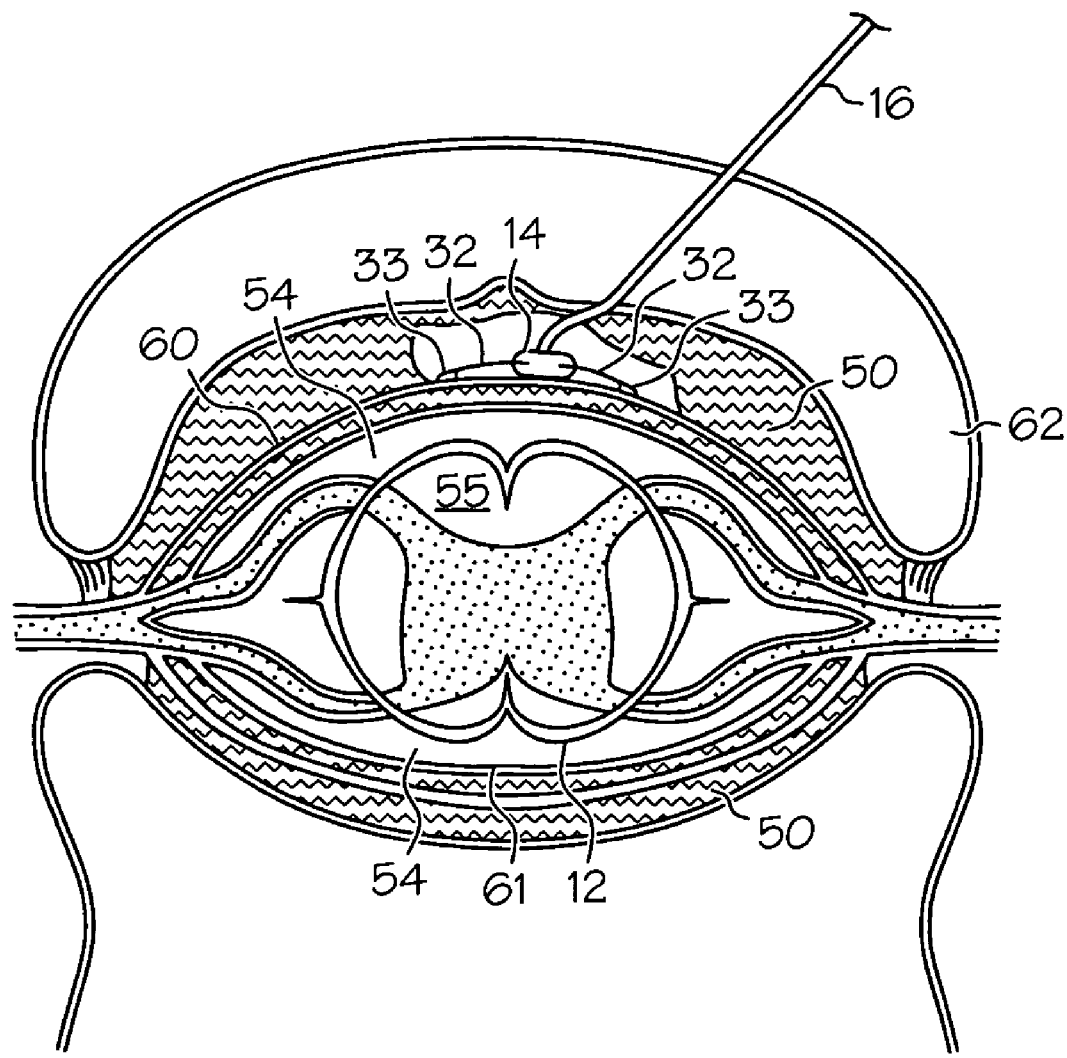
FIG. 2 is a cross sectional view of the spinal cord showing implantation of a preferred lead.

FIG. 2 is a cross-sectional view of spinal cord 12 showing implantation of the distal end 14 of the lead 16 within the epidural space 50. Also shown for purposes of orientation are the dorsal columns 55 of the spinal cord, the dura mater 60, the vertebral bone 62, the arachnoid membrane 61 generally adherent to the dura mater, and the intrathecal space 54 containing CSF. The distal tip 14 has two extendable members 32 deployed laterally, and each has one electrode 33 on its distal tip. As an extendable member 32 is passed distally, out the tip 14 of the lead, its most distal part, no longer constrained by the confines of the lead body, will curl up due to preset elastic properties and form a 2-or 3-dimensional electrode 33. If the extendable member 32 is pulled back into the lead tip 14, each electrode 33 will uncurl and straighten out again.

Figure 3:
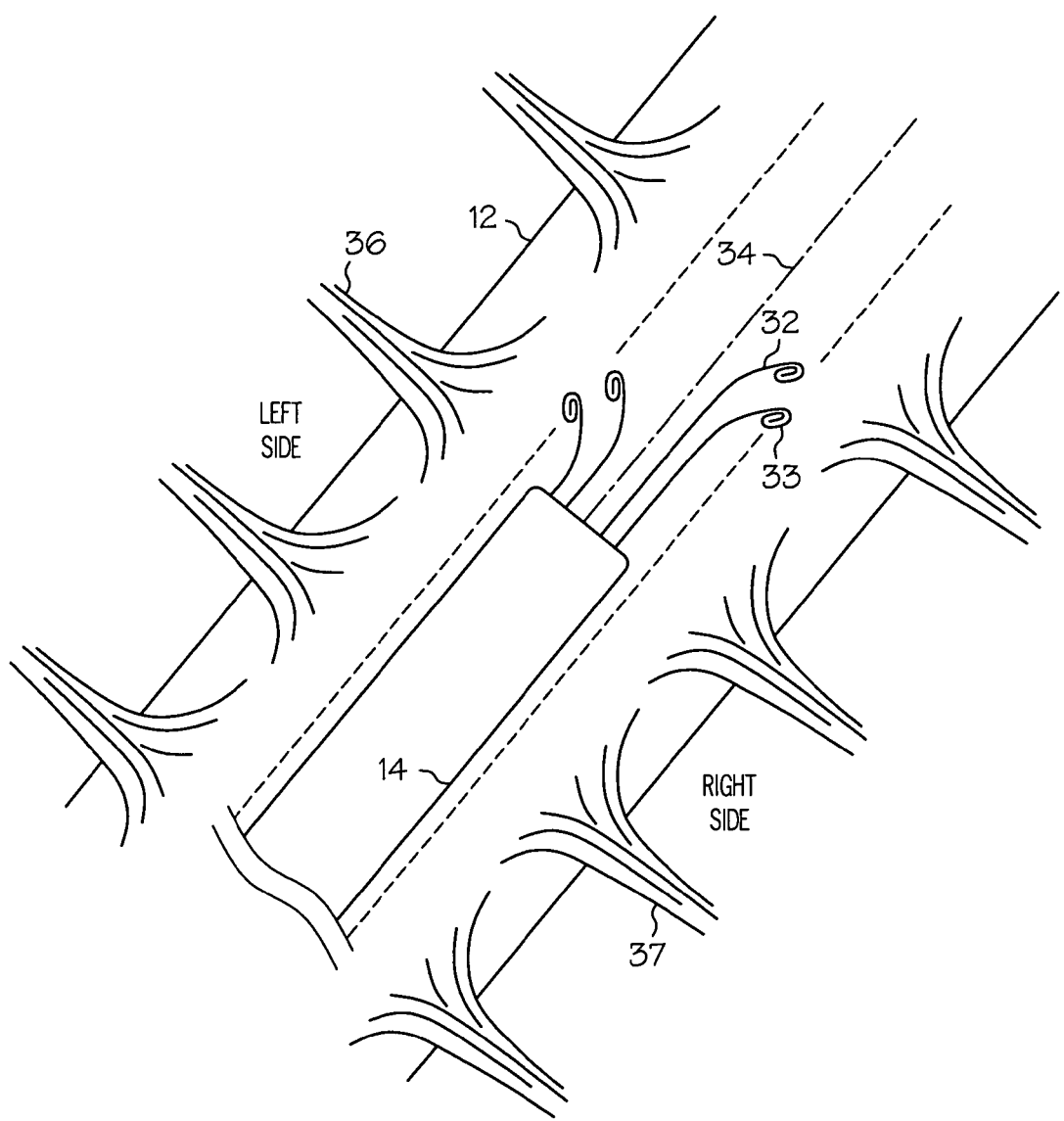
FIG. 3 is a coronal view of the dorsal surface of the spinal cord showing the distal end of an implanted lead.

FIG. 3 is a coronal view (from the top, if patient lies on stomach) of the dorsal surface of the spinal cord 12 showing the distal end 14 of an implanted lead. The lead's distal ending 14 is placed near the midline of the spinal cord 34, parallel to the cord. Left dorsal roots 36 and right dorsal roots 37 are shown as if the dura mater was transparent, passing further laterally off the dorsal surface of the spinal cord. The distal tip of the lead 14 has a narrow width, capable of passing through the lumen of a Tuohy needle, typically 14 to 15 gauge. There are four electrodes 33 depicted. Each one is formed from a curling of the tip of one extendable member 32 after it has passed out of the lead's distal tip 14. Notice that due to other preset elastic properties of the extendable member 32, as it is passed beyond the narrow confines of the distal tip 14, it will curve laterally, allowing the electrodes 33 to be located much more laterally than the diameter of the lead body. The degree of exposed curvature, hence the lateral position of the electrodes 33 can be controlled in two ways: 1) by only extending the members a small distance out of the lead tip 14 depicted for the two members on the left, or, 2) by extending them beyond the portions of each extendable member that are preset as curved, as depicted for the two members on the right, in which case the maximum possible lateral position is achieved for that member and its electrode. Also, by passing the two members on each side a variable distance past the tip of the lead body 14, the electrodes on each side can be placed at different spinal levels.

Figure 4:
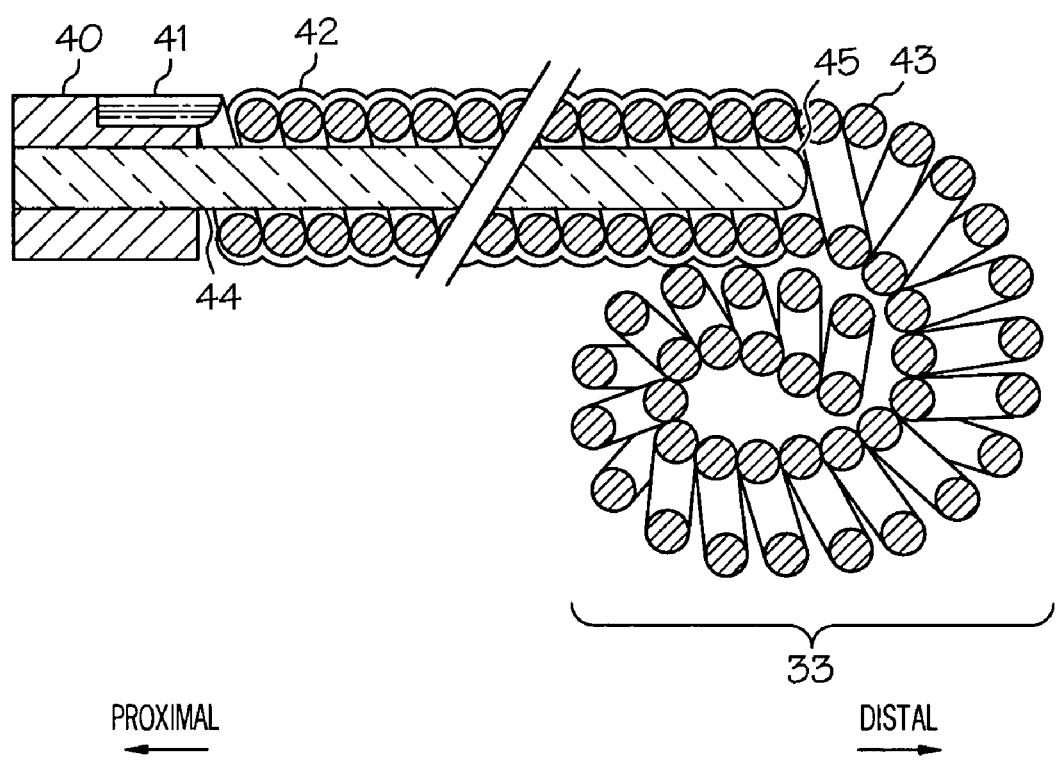
FIG. 4 is a cross-sectional view showing both ends of an extendable member used with the lead.

FIG. 4 depicts a cross-section of the proximal and distal ends of one of the extendable members that can be slid in or out of the end of the lead 14. The member has an electrically conducting metallic coil 43 running its entire length. This allows it to be very flexible, which is advantageous for the member to stay close to the dura mater in spite of great flexibility of the spine, especially in the cervical area. However, as the extendable member is pushed out of the distal tip of the lead 14, it needs sufficient stiffness and direction so that its motion is in a desirable direction, such as lateral. An internal wire 44 inside the spring 43 in one or more portions of the extendable member is able to give this direction and stiffness.

Near the distal end of the member, the internal wire 44 has a distal tip 45, and extending beyond that is only the coiled conductor electrode 33. This part of the conducting coil has been prestressed, by heat, pressure or chemical treatment or by use of bimetallic metals or nitinol material, so that once the end of the member is beyond the tip of the lead 14, it will curl back upon itself at least one time, creating a two-dimensional circular, oval or rectangular pad or electrode 33. If the extendable member were retracted back into the lead tip 14, the curled portion would straighten again inside the lead tip 14. Hence, this member can be easily retracted from the body merely by pulling it back into the lead body. The entire epidural lead, in spite of having sizeable 2-dimensional electrodes, can be removed from the epidural space by pulling it out. This is an advantage that conventional paddle leads do not possess.

There is insulation 42 on all outer surfaces of the extendable member except in two sites. One is the proximal end 40. This part is a conductive metal, such as stainless steel, to which a proximal end of the conductor coil 41 can be welded. This proximal end can fit into an electrical receptacle such as an extension or the pulse generator itself, so that electric currents can be passed into the member. The insulation 42 prevents leakage of current except at the other end of the member, beyond the tip of the internal wire 45, where the conductor coil 43 is also not insulated, and becomes curled into the pad-like electrode 33 once the member's tip is deployed in the epidural space. Due to the prestressing, the conductor coils at the tip electrode 33 might not have the same size, shape or consistency of the conductor coils more proximally.

The electrically conductive area of this electrode 33 should be large enough to allow therapeutic electric currents (typically up to 20 ma) to pass at voltages available from the implanted pulse generator (typically up to 15 Volts). Hence, enough of the distal end of the extendable member must be uninsulated so that the impedance of the member from proximal to distal end is less than 500 Ohms, and potentially less than 100 Ohms, since other parts of the system like the extension and pulse generator and the tissue itself may also have impedance that restricts the amount of current to flow.

The exposed, uninsulated electrode 33 is typically made of robust and nonreactive materials, like the metallic electrodes of commercially available implanted stimulation leads, which often use platinum or platinum/iridium blends. If the entire impedance of the extension and conductive members and tissue paths is 500 Ohms, and the implanted power source delivers 10 Volts, the current that flows is 20 milliamperes. If the electrical signal is composed of substantially square wave pulses, with a 200 microsecond duration, for example, then each pulse delivers 4 microCoulombs of charge (Current× pulse width). The charge density at an electrode of exposed surface area 8.0 square millimeters is thus 50 microCoulombs/ square centimeter/pulse. This is below the charge density at which pure platinum or platinum/iridium electrodes cause production of oxygen or hydrogen gas at their surface, which would soon cause damage to the electrodes or tissue (Table 2.4, page 57, in *Neural Prostheses: Fundamental Studies*, ed. W. F. Agnew and D. B. McCreery, Prentice Hall, Englewood Cliffs N.J., 1990). Considerations like these must be used to design and build the coiling electrodes that have enough surface area to be safe and reliable. In addition, each electrode should have a tight-enough curl and orientation so that the area of that electrode presented toward the surface of the nervous tissue being activated, is reasonably compact. This area is typically at least 6.0 and at most 24.0 square millimeters, at least for epidural SCS.

Figure 5:
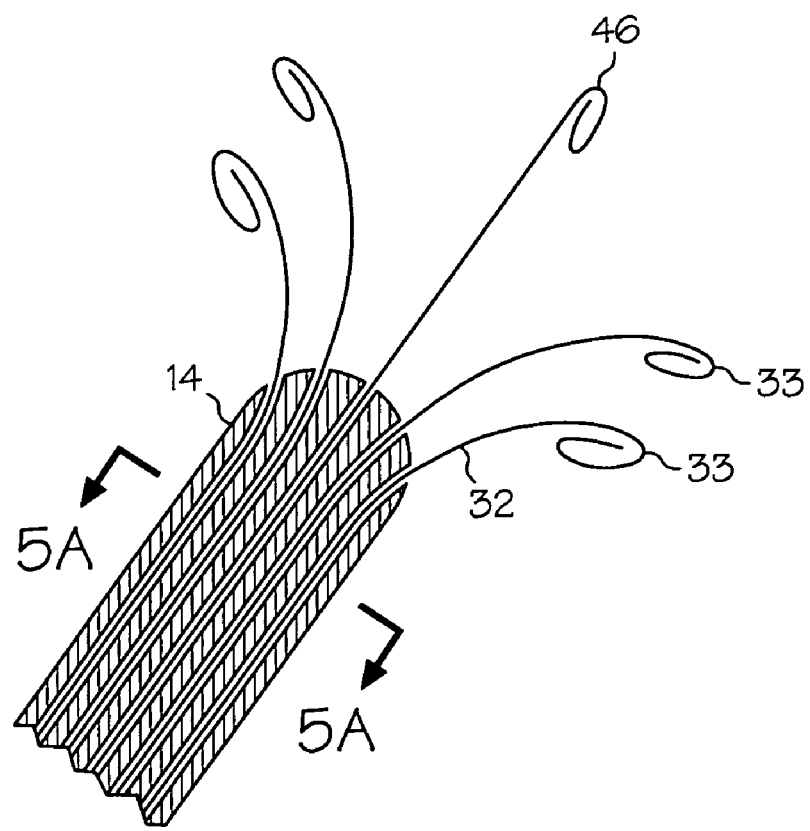
FIG. 5 is a cut-away view of the distal end of an implanted lead, with a cross-sectional view, FIG. 5A, of the epidural portion of the lead.
Figure 5A:
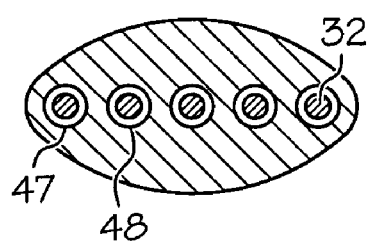

FIG. 5 is a cut-away view of the distal end 14 of an implanted lead with extendable members 32 deployed, and FIG. 5A is a cross-sectional view of the epidural portion of the lead. Each member 32 can be extended beyond the lead tip 14 and it will gently curve to allow lateral positioning of electrodes 33 or not, as shown by a midline electrode 46, depending upon whether that particular member has a preset curve. The curve is due to preset elastic properties of the internal wire 44 of FIG. 4. Section 5A-5A is an axial cross-section of a portion of the distal end of the lead 14. As depicted, there are five channels, with two of them labeled 47 and 48, each one with an extendable member 32 that may be slid back and forth, except when there is an anchor placed to prevent movement of the member relative to the lead body. Such an anchor may be simply a suture tied by the implanting physician tight enough to compress the lead body around the members, or may be more elaborate with set screws, collars, etc. In another embodiment, there may be designed an asymmetric feature in both the member and its channel so that each member has a fixed alignment relative the lead body. This would make the curving of the extended parts of the member predictable, as shown in FIG. 5, where the electrodes lie in a nearly planar array that may be next to the dura. Note that the cross-section 5A-5A is not circular. While Tuohy needles are widely available, more recently other shapes of hollow needles are being considered for epidural placement of leads, and these may allow slightly larger cross-sectional areas, or shapes that are not only circular.

An alternative design would not require an individual channel for each extendable member, but rather a single lumen in the middle, or one lumen for several members that will curve toward a given side. The implanting physician could selectively pass each member out the tip of the lead 14, and would use fluoroscopy to determine the direction of curving and lateral motion, using rotational torque on each member to optimize its position. However, either such a multi-member channel would be narrow enough to prevent curling of the tips inside the lead body, or, should the tips curve and bend backwards inside the channel, the tips must be sufficiently flexible and the stiffening wires sufficiently strong to still pass the member distally, whereupon the tip 33 will form complete and adequate 2- or 3-dimensional pads or electrodes.

Figure 6:
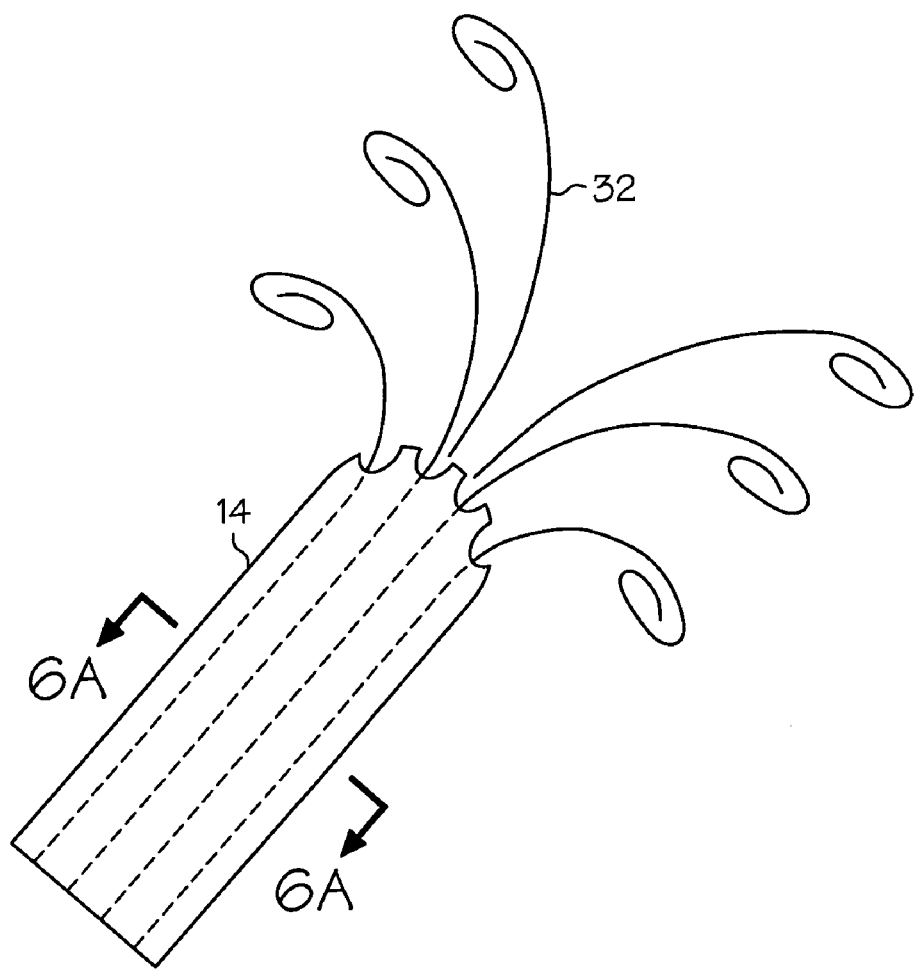
FIG. 6 is a view of the distal end of an implanted lead, with a cross-sectional view, FIG. 6A, of the epidural portion of the lead showing another embodiment.
Figure 6A:
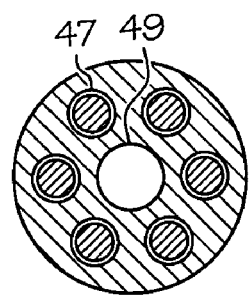

FIG. 6 is a view of the distal end of an implanted lead 14 with members 32 deployed outwardly. FIG. 6A is an axial cross-sectional view depicting another embodiment, Section 6A-6A. This view shows six channels 47 for passage of extendable members 47, and a central open lumen 49, which can be used for a stylet to help in initial positioning of the lead body in the epidural space. Such a stylet is typically removed prior to closing all incisions in the patient because it is too stiff to leave there permanently. A symmetric, hexagon shape for the location of these channels is one way to best use the available space in the lead body, but other positions are possible, especially if the axial cross-section shape is not circular.

Figures 7, 7A:
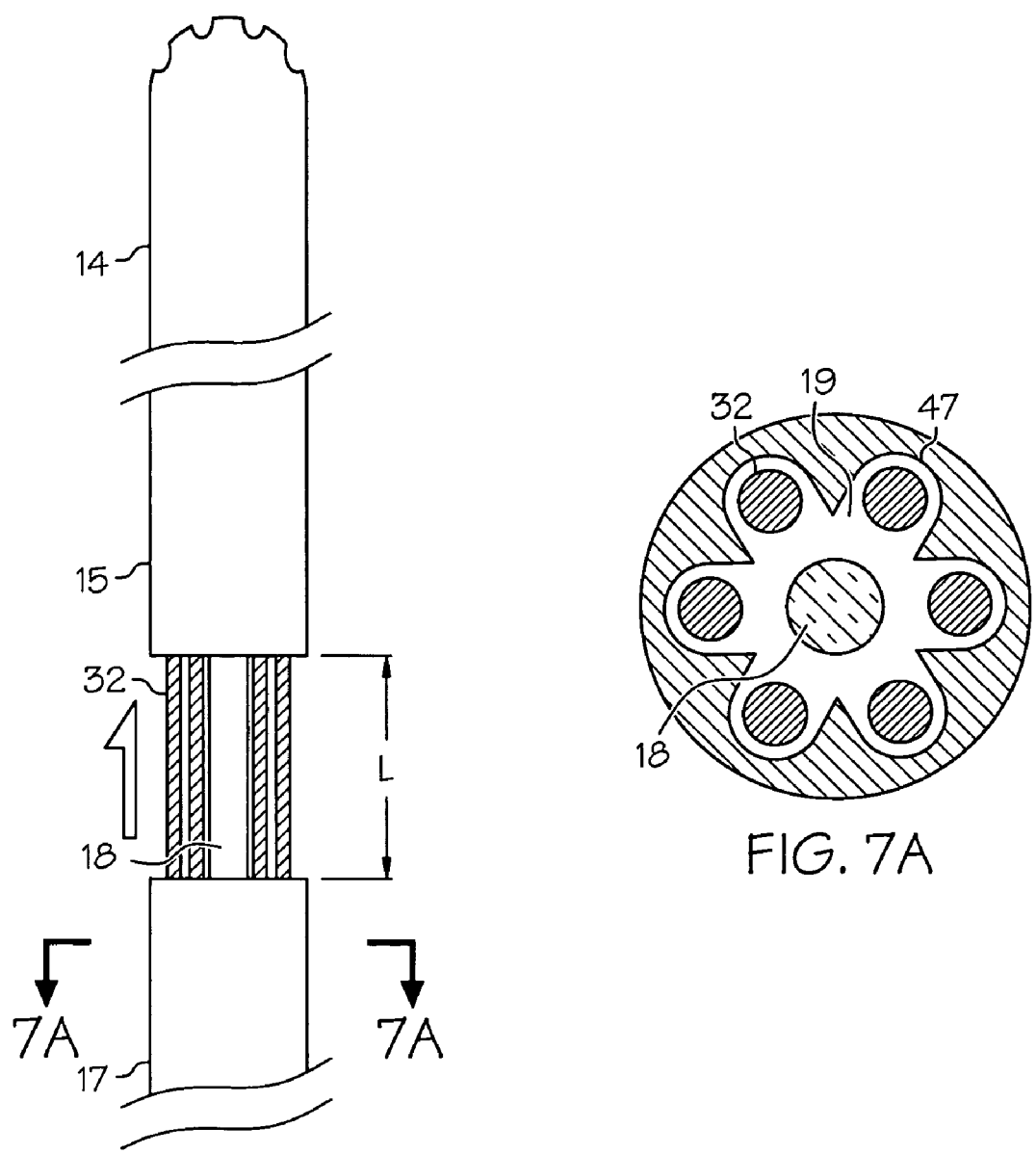
FIG. 7 is a side view of the surface of the implanted lead, showing the distal tip and a middle portion when the electrodes are not yet deployed, and a cross-sectional view, FIG. 7A, of a middle portion of the lead.

FIG. 7 is a side view of the surface of the implanted lead, showing the distal tip 14 and a middle portion 15 when the electrodes are not yet deployed, and another portion 17 that is more proximal. When the middle portion is in the depicted position, with separation "L" between portion 15 and portion 17, the extendable members 32 are still inside the distal tip 14. By design, this gap should be located along the lead body so that its position will lie in the skin incision where the implanting physician can access it. Members 32 are attached permanently to lead body portion 17. When ready to deploy the members 32, the physician will hold the portion 15 steady with an instrument, and will push the portion 17 forward to close the gap "L". This will simultaneously slide all six extendable members 32 distally, with their tips extending out of the distal tip 14 of the lead body. In another embodiment, lead body portion 17 may have several independent parts, each one to be able to deploy one or more members independently. Section 7A-7A, as depicted in FIG. 7A, is an axial cross-section of portion 17 near to the gap "L". It shows six members 32, each in their own channel, although the channels may be open to a central lumen 19. There is a stylet 18 in the center. It may be later removed to allow greater flexibility of the lead, or it may remain. In this embodiment, if the channels open up to a central lumen 19, the stylet 18 may serve the function of keeping each member 32 in its channel, due to its adequate diameter.

Figure 8:
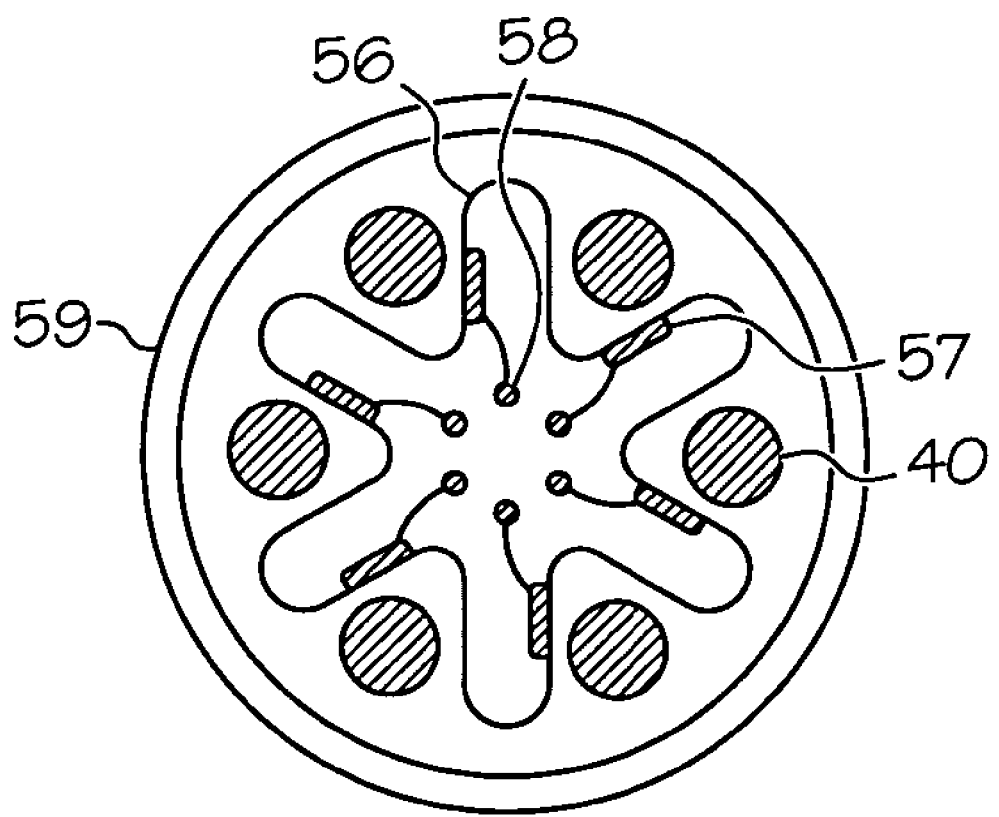
FIG. 8 is a cross-sectional view of an electrical receptacle of an extension or power source into which the proximal ends of each of the lead's six deployable members may be electrically grounded.

FIG. 8 is a cross-sectional view at the level of the most proximal ends of the extendable members 40, where electrical connections are made to a receptacle 56 of either an extension or implanted pulse generator. The view depicts six of the proximal endings of members 40, as shown in FIG. 4. Each one can be placed or pressed into an electrical connector, which has a conducting electrode 57, and each of these in turn has a wire 58 that is the source of electrical signal from the next component of the system. The member's proximal ending 40 can have a secure electrical communication with the electrode 57 either by use of set screws or Ball-seals®, like current commercially-available electrical systems, or can be held into position by the depicted elastic band 59, as shown. This connection must also have the flanges of the electrical receptacle 56 seal against the surrounding elastic band 59, which is an insulator like silicone rubber, so that current will not leak from one conducting electrode 57 to the next one. Either the elastic band 59 or another insulated boot must go over these connections to permanently seal out ionic solutions, which might short out the signals.

In the design of FIG. 7, all six proximal endings of the extendable members 32 will have the same longitudinal position along the lead body, and hence the electrical receptacle 56 in FIG. 8 may have a short axial length to will accommodate all of the member's proximal endings 40. However, if each extendable member is advanced by itself or in groups to varying degrees, there will be intra-lead redundancy in the lengths of the members that must be handled at the site of the electrical receptacle 56. In another embodiment of the connection described in FIG. 8, the axial length of the receptacle 56 and its electrodes 57 are long enough to handle this redundancy. Alternatively, redundant intra-lead lengths of extendable members are looped or bunched up under an insulated elastic band 59 or insulated boot, which may also be filled with silicone rubber for added insulation. All of these connections may be made in a subcutaneous pocket, where there is some leeway for size. If the lead must be removed or replaced, or the extendable members repositioned, surgical access to this pocket is necessary, regardless of the type of lead used.

Figure 9A:
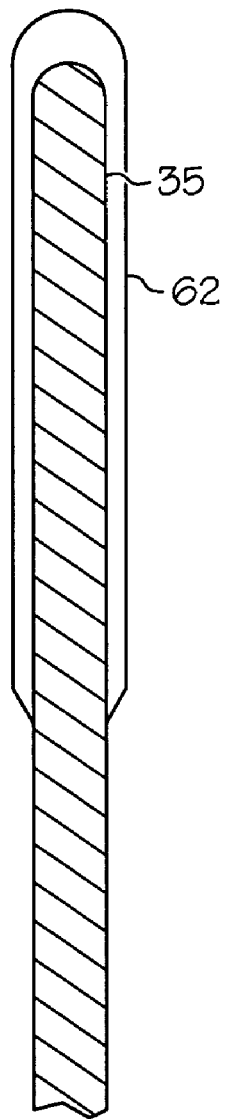
FIGS. 9A and 9B show two views of the distal end of a another embodiment of the lead, with FIG. 9A illustrating the distal end a dissolvable covering material that keeps it straight, and FIG. 9B illustrating the distal end after dissolution of the covering material, with the tip curled into a two-dimensional electrode.
Figure 9B:
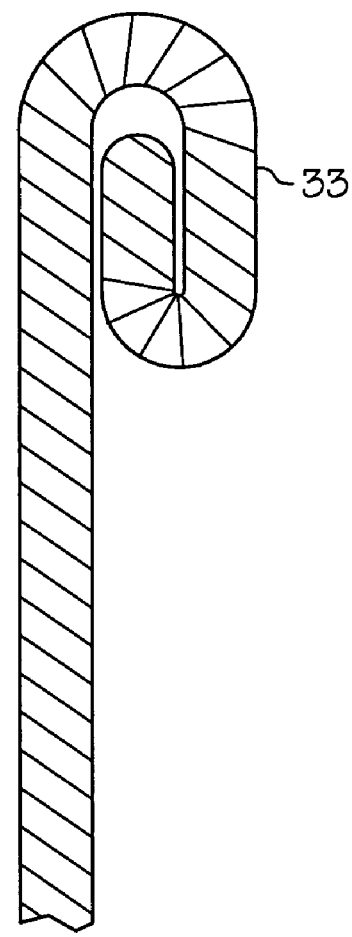

FIG. 9 shows two views of the distal end of a lead of another embodiment to help deployment of the extendable members and placement of the electrodes. In FIG. 9A, the conducting tip of the member, which will eventually have a curl, is straight 35 while the member's tip is still inside the lead body, or while it is being deployed in directions determined by the preset curvature of the member. This degree of straightness is caused by a thin but strong coating 62. This coating may be made from a wide variety of materials that are nontoxic, and which will dissolve in a matter of minutes to hours. The coating will enable the straight tip of the member 35 to poke through adhesions or fibrosis, with minimal deflection. After this coating has dissolved, FIG. 9B shows that the conductive tip of the member can curl up to form the conducting electrode 33. The coating may be pointed in shape, to make deployment easier. Since the member's tip 35 is metallic, it will be easily visible on fluoroscopy. In another embodiment, if there is a bimetallic metal component or nitinol is used to curl and uncurl the member's tip, controlled with the use of electric currents, then the transition from curling to uncurling can be done repeatedly, or electively only when there are obstructions that make positioning of the member's tip difficult.

Figure 10:
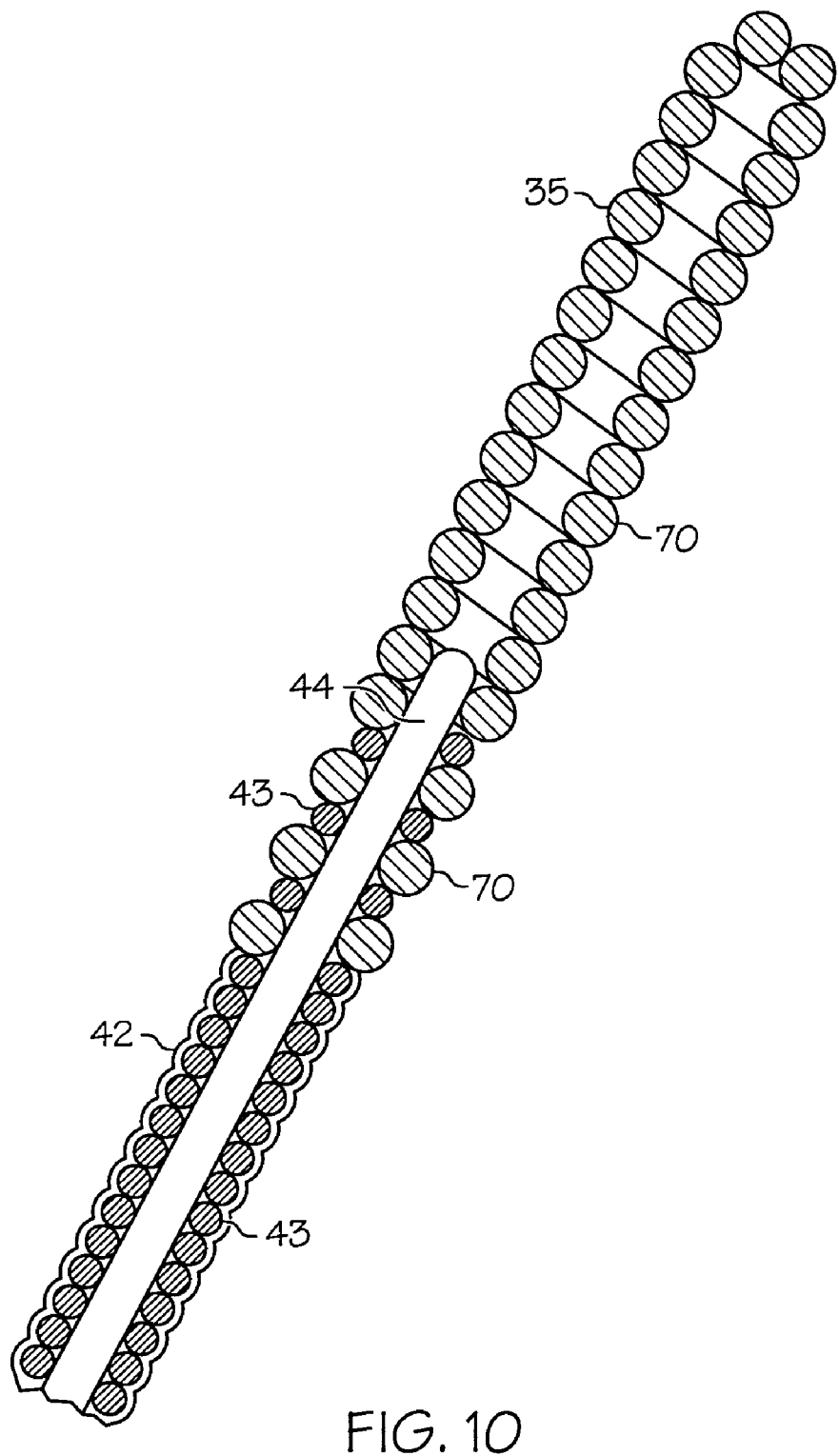
FIG. 10 is a cross-sectional view of the distal end of another embodiment of an extendable member, prior to deployment, showing how two dissimilar springs can be attached to allow different mechanical characteristics.

FIG. 10 is a cross-sectional view of the distal end of an extendable member 35 of another embodiment of the invention, prior to deployment. FIG. 10 shows how two dissimilar conductor coils can be attached to allow different mechanical characteristics. The proximal coil 43 goes from the proximal end out to a position near the end of the internal wire 44. It carries the electric signals, and is insulated 42 except for the proximal end where it has electrical connection to the extension or implanted pulse generator. A dissimilar coil 70 begins at the end of the first spring 43 or is intertwined partially in the coils of the first spring as shown, and constitutes most of the member tip that will curl to form an electrode. The tip coil 70 will have the preset properties that allow it to curl once the member is deployed out of the lead body, and may be considerably more flexible than the proximal coil 43. Use of two dissimilar conductor coils may be useful, especially since one, coil 42, needs a low impedance, and the other, coil 35 may need the ability to accept a preset coiling tendency.

Figure 11:
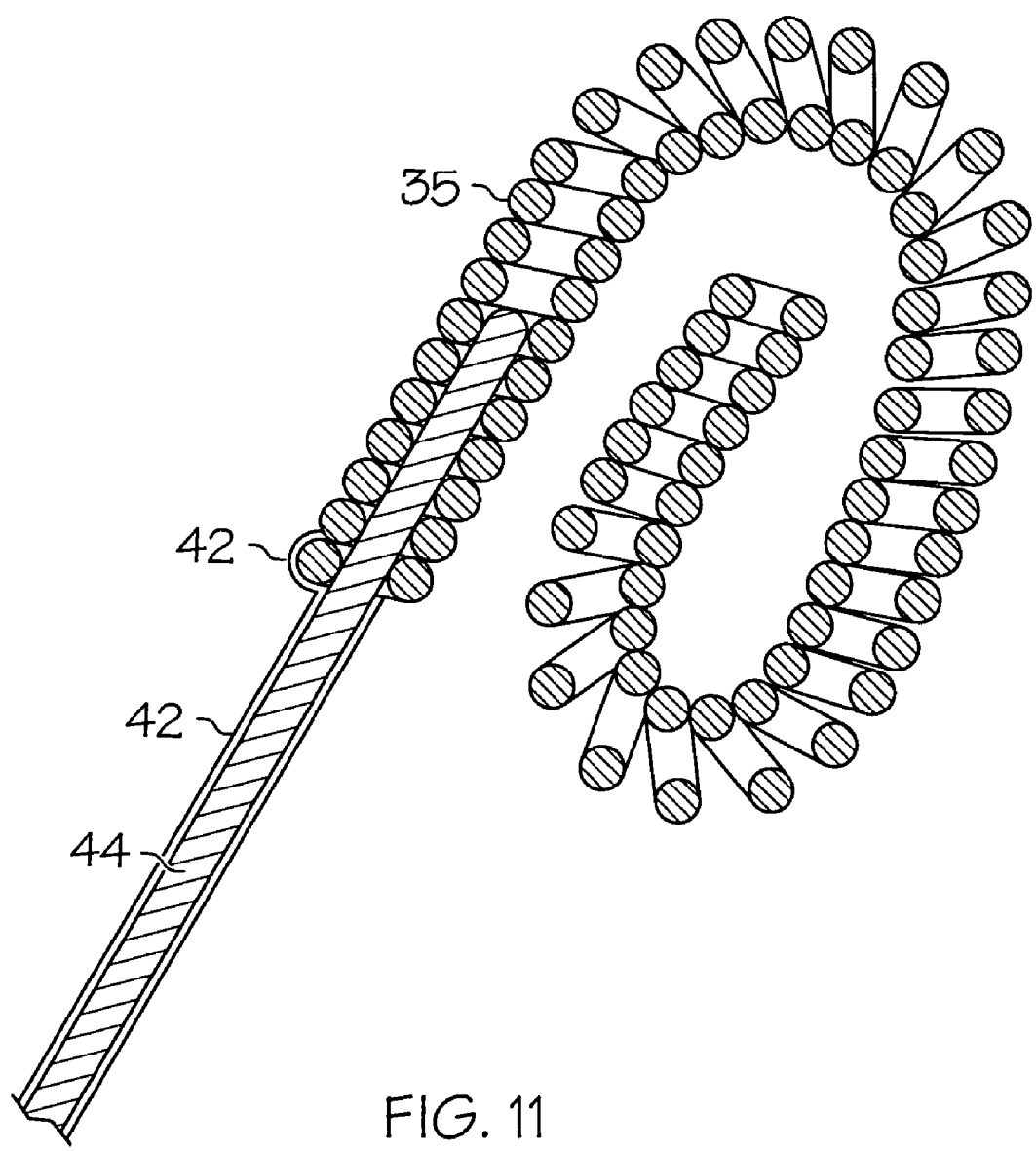
FIG. 11 is a cross-sectional view of the distal end of another embodiment of an extendable member after deployment, showing how a spring-like ending, which is not insulated, can be attached to an insulated proximal wire portion.

FIG. 11 is a cross-sectional view of the distal end of another embodiment of an extendable member of the invention after deployment, showing how a conductor coil ending that is not insulated can be attached to an insulated proximal wire portion. Here any proximal conductor coil from the most proximal tip of the member is not needed. The wire 44 comprises the member itself proximally, and has an insulative coating 42. Attached to the distal end of this wire 44, both mechanically and electrically is a member tip 35 that will curl to form a 2-dimensional electrode after deployment. Most of this member tip 35 is not insulated.

Figure 12:
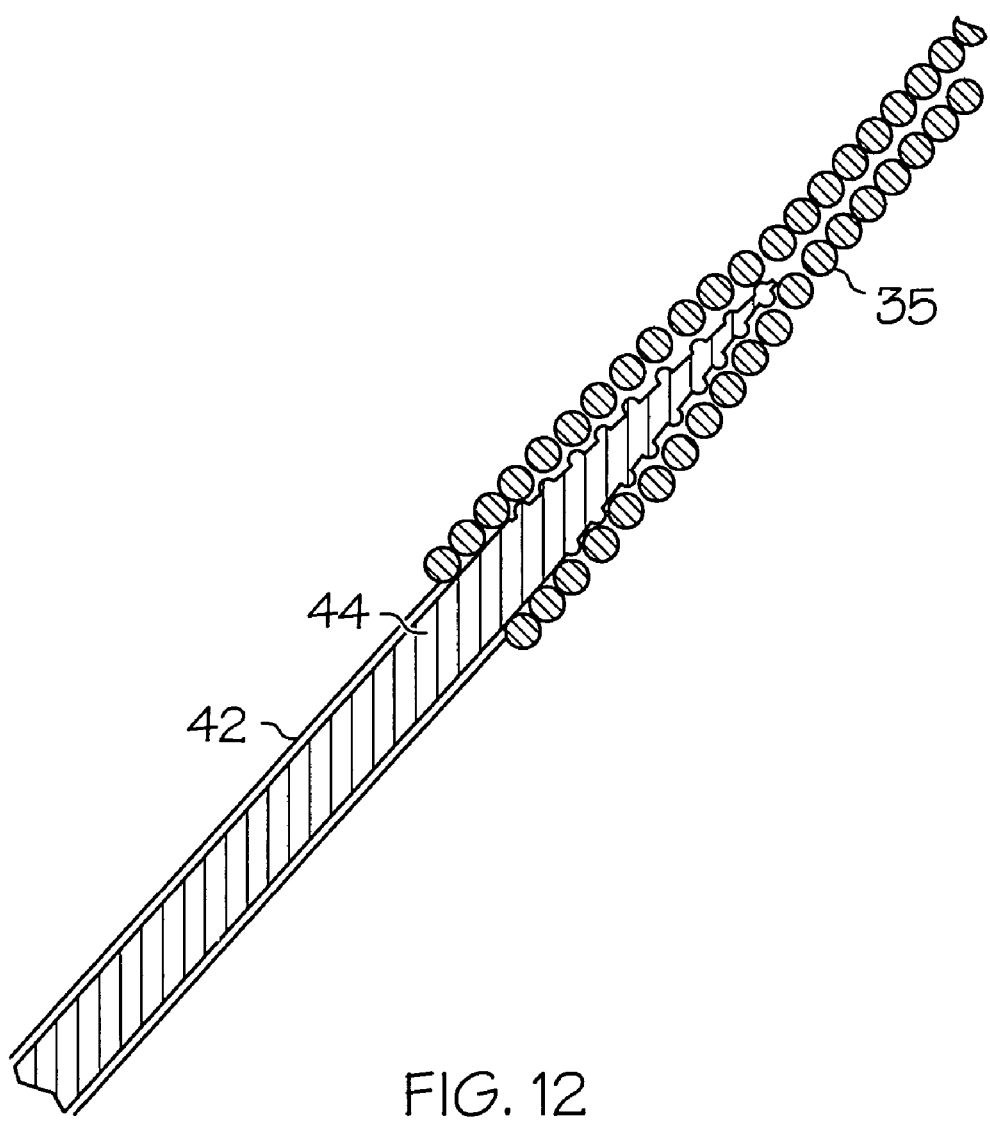
FIG. 12 is a cross-sectional view of a portion of an extendable member near the distal end prior to deployment, showing how a spring-like coiled conductor ending, which is not insulated, can be screwed onto an insulated proximal wire portion.

FIG. 12 is a cross-sectional view of a portion of an extendable member near its distal end, prior to deployment, showing how a conductor coil ending 35 that is not insulated can be screwed onto an insulated proximal wire portion 44. This is a most convenient way to assemble the tip of the extendable member. As the ending 35 curls to form a 2-dimensional electrode, one edge of this electrode will be the conductor coil that is screwed onto the threaded wire tip.

Figure 13:
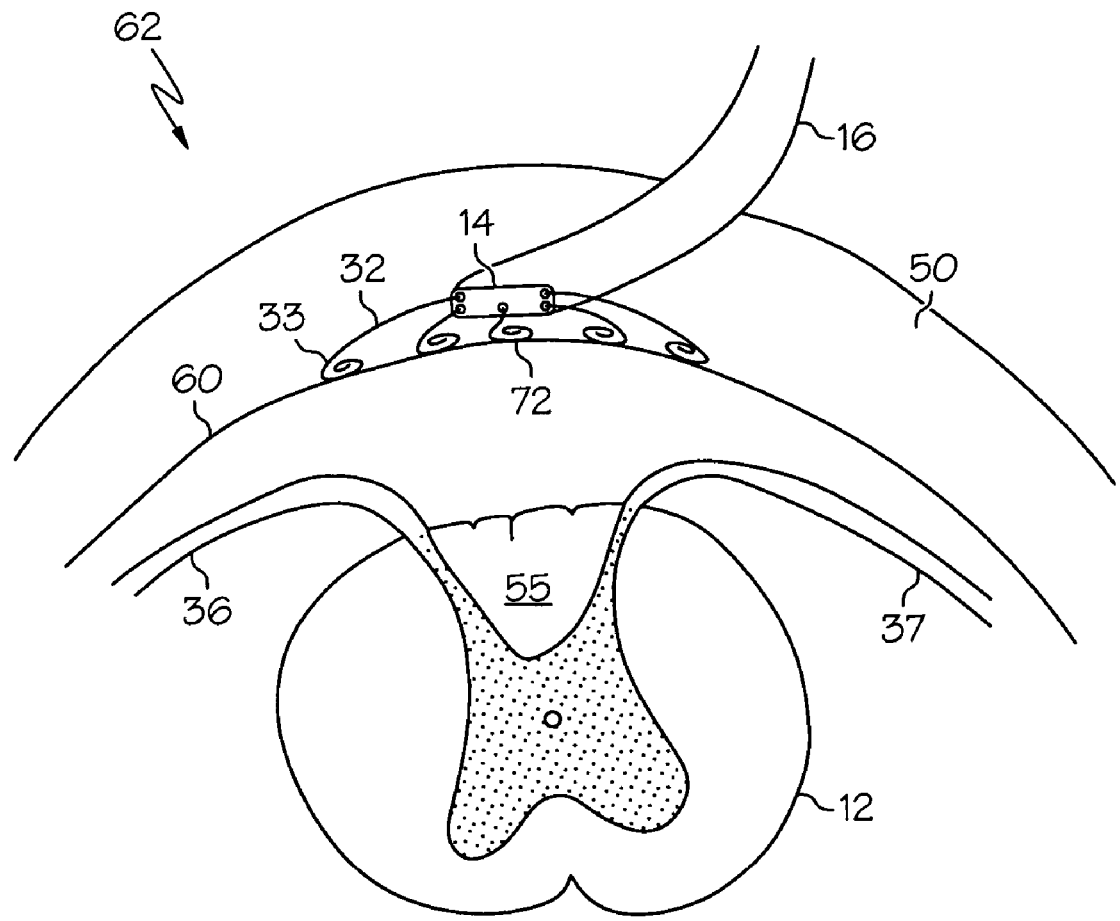
FIG. 13 is a cross-sectional view of a lead portion near the distal end showing how five electrodes can be positioned at various lateral and ventral positions to match the shape of the dura.

FIG. 13 is a cross-sectional view of a lead portion 16 near the distal lead end 14 showing how five electrodes 33 can be positioned at various lateral and ventral positions and match the shape of the dura mater 60. In this example, one electrode is fixed to the tip of an extendable member that passes straight out of a central channel and has a slight ventral curve 72. This curve can be modest, if the lead end 14 is close to the dura, or it can be much sharper, if the lead end 14 is nearer to the vertebral bone 50. The other four electrodes 33, are located on members that curve both laterally upon deployment and also ventrally. The degree of ventral curve can be matched to the shape of the dura mater 60 at that particular lateral position. In this way, the electrodes can be positioned up against the dura mater 60, allowing electrical efficiency due to less impedance, since the impedance of the epidural space 50, filled with fat or blood vessels, is substantial more than the impedance of the CSF in the subdural space.

Figure 14:
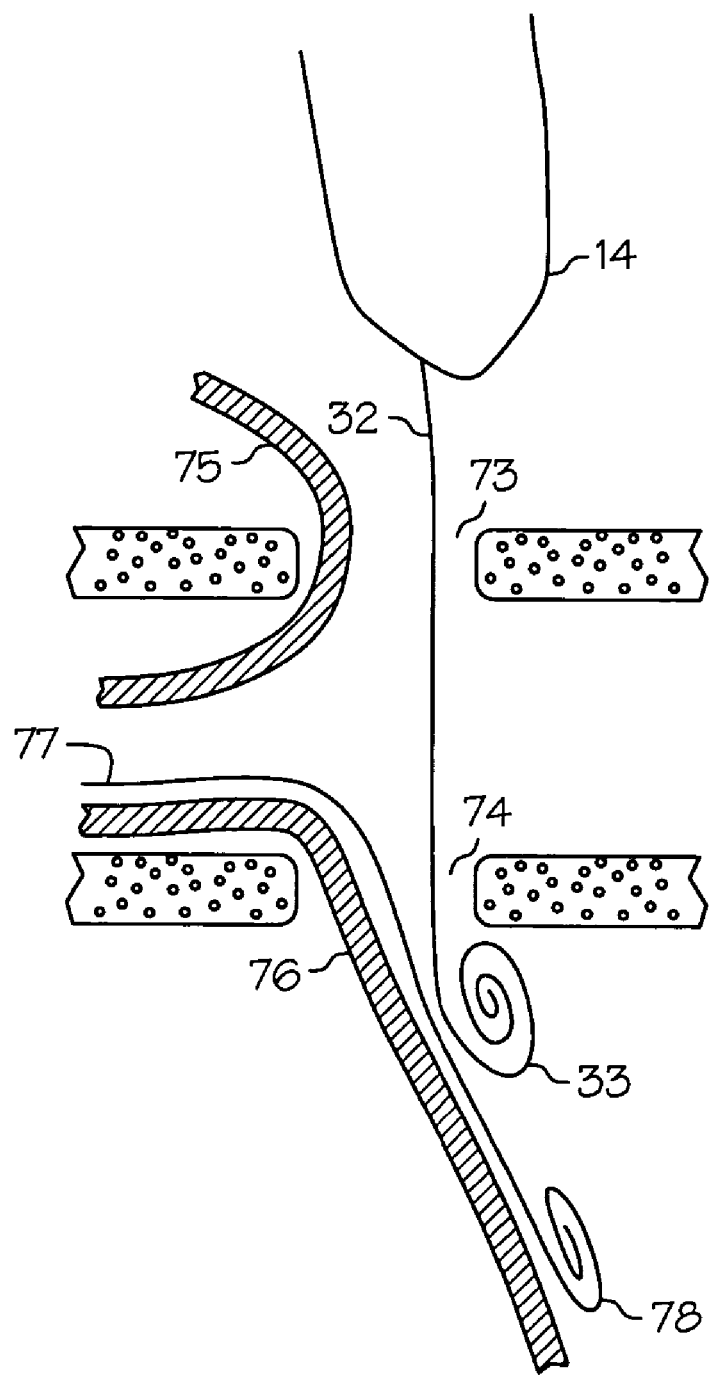
FIG. 14 is a cut-away view of a the distal tip of a lead body, with one extendable member passing through a sacral foramen and another following a sacral nerve, allowing placement of electrodes near a peripheral nerve.

FIG. 14 is a cut-away view of a the distal tip of a lead body 14, showing two embodiments that allow the safe introduction of electrodes near to delicate and small peripheral nerves. The view shows a dorsal sacral foramen 73 and a ventral sacral foramen 74, which are holes in the sacral bone that allow nerves to pass into the body. Two nerves are shown, a dorsal sacral nerve 75, for example the S3 nerve, and a ventral sacral nerve 76, going inside the pelvis to visceral organs and muscles. Often, screening leads are placed in or through the ventral sacral foramen 74, to see if urinary incontinence can be improved or visceral pain lessened. If there is success, then percutaneous-type permanent leads with electrodes are placed, but they often no longer give as much therapeutic benefit. This could be improved if the physician could implant a larger electrode near the ventral sacral root 76. Preferred embodiments of the invention make it possible to place a larger electrode near the root than the spaces through which that electrode must be passed. In one method, a lead tip 14 is placed over the dorsal ventral foramen 73. One or more extendable members 32 is passed through both sacral foramena, and its tip 33 can curl into an electrode whose dimensions can be larger than the diameter of the accessible lumens. Some physicians today pass standard percutaneous SCS leads caudally, following a ventral sacral nerve 77 from inside the sacral bone through the ventral sacral foramen 74. This may be dangerous since each sacral root nearly fills up the lumen of its passage near and through the ventral sacral foramen 74. An alternative method using the invention would have the physician pass an extendable member 77 from above, also the side of the ventral sacral nerve 76, and out of the ventral sacral foramen 74. In that foramen, or beyond, the electrode 78 can curl. The extendable member 77 can be of a very small diameter so there is room next to the ventral sacral nerve 76, and the electrode can form in a space where there is adequate room.

Thus, preferred embodiments of the invention allows introduction of an electrode through a smaller lumen in the body.

On the other side of the lumen, the tip can curl into its preset shape and become a 2- or 3-dimensional electrode. If necessary in the future, simple traction upon the lead body or each extendable member will allow the tips to uncurl and retract through the narrow lumen. A good example of this application is placement of an electrical electrode through a vertebral or sacral foramen for peripheral nerve stimulation of a particular nerve outside the vertebral bones. A larger, 2-dimensional electrode has a better chance to have a stable excitation of a nerve than a percutaneous-type electrode with a 1.0 mm width. Placing two such electrodes along one nerve may also be desirable, both to be sure to excite the axons in the nerve by one or both of the electrodes, and to stimulate across the nerve with one electrode on either side, if one is a cathode and the other an anode. Another useful application is to treat trigeminal neuralgia, wherein the lead body or member is passed through the foramen rotundum of the cheekbone into the space of Gasserian ganglion.

While the above examples show use of preferred embodiments of the invention for stimulation of spinal cord or peripheral nerves, the same techniques can be used for stimulation of any excitable tissue where there is sufficient space for the tips of the extendable members to curl into electrodes, e.g., inside the ventricles of the brain or on any surface of the brain. Such methods may be very advantageous when very flexible but removable electrodes are needed, for example, in intrathecal or subdural stimulation. On occasion, sufficient space can be created through prior use of dilators, especially for stimulation on the surface of muscles or subcutaneously.

While the preferred aspects of the invention have primarily been described with respect to use of medical or implantable medical leads used for electrically stimulating tissue, such as nervous tissue, it will be understand that such medical leads may also be employed for sensing or monitoring physiological parameters, such as for example electrical activity within the spine or brain.

Those skilled in the art will recognize that the preferred embodiments may be altered or amended without departing from the true spirit and scope of the invention, as defined in the accompanying claims.

What is claimed is:

1. A kit comprising:
    a needle; and
    an implantable lead for stimulation of nerve tissue, muscle or organs, wherein the implantable lead is adapted to be passed through the needle, the lead comprising:
        an elongate lead body having an axis, a tip, and a channel, wherein the channel has an asymmetric cross section; and
        at least one extendable member having a distal portion adapted to curl upon itself when not-constrained to form an electrode, a proximal portion, and an asymmetric cross section that engages the asymmetric cross section of the channel to hold the extendable member against rotation relative to the lead body, the extendable member received at least in part within the lead body for axial movement between:
            a retracted position in which the distal and proximal portions are constrained within the lead body; and
            an extended position in which the proximal portion is retained within the lead body and the distal portion is deployed out the tip of the lead body such that the distal portion curls upon itself to form an electrode.

2. The kit of claim 1 in which the extendable member further comprises an intermediate portion between the distal and proximal portions.

3. The kit of claim 2 in which the intermediate portion is deployed out of the lead body when the extendable member is in the extended position.

4. The kit of claim 2 in which the intermediate portion comprises an insulated wire allowing current to flow between the proximal portion and the distal portion.

5. The kit of claim 2 wherein the intermediate portion is adapted to curl as it is deployed out the tip of the lead body less tightly than the distal portion curls upon itself.

6. The kit of claim 5 in which the distal portion is formed such that it tends to curl upon itself in two dimensions in the extended position.

7. The kit of claim 5 in which the distal portion is formed such that it tends to curl upon itself in three dimensions in the extended position.

8. The kit according to claim 1, wherein the extendable member comprises wire, and the distal portion comprises one or more external coiled conductors.

9. The kit according to claim 8 wherein the one or more external coiled conductors comprises a plurality of external coiled conductors having dissimilar properties.

10. The kit according to claim 1, wherein the distal portion of the extendable member has preset elastic properties that tend to cause the distal portion to curl into an electrode.

11. The kit according to claim 1, wherein the distal portion of the extendable member is formed of bimetallic metals or nitinol material that change shape due to temperature changes.

12. The kit according to claim 1, wherein the distal portion of the extendable member will uncurl if the extendable member is retracted into the lead body.

13. The kit according to claim 1, wherein the distal portion of the extendable member is sufficiently flexible that the distal portion will uncurl if the entire lead body is pulled through tissue, thereby reducing trauma to the tissue if excessive forces are applied to the lead.

14. The kit according to claim 1, wherein the extendable member has a preset curve so that as it is extended axially beyond the lead body, it will move also in directions laterally to the axis of the lead body.

15. The kit according to claim 14, wherein the extendable member has a preset curve over the distal portion.

16. The kit according to claim 14, wherein the extendable member has an elasticity that allows it to be held straight by the lead body but allows the extendable member to resume its preset curve when it is extended beyond the tip of the lead body.

17. The kit according to claim 14, wherein the extendable member has a preset curvature such that, when deployed out of the lead body, the extendable member moves in axial directions and lateral directions.

18. The kit according to claim 14, wherein the extendable member has a preset curve so that as it is extended beyond the lead body, it will move also in directions perpendicular to the axis of the lead body.

19. The kit according to claim 1, wherein the extendable member comprises a plurality of extendable members, each of which can be independently extended to deploy a distal portion beyond the tip of the lead body.

20. The kit according to claim 1, wherein the lead body has a diameter, and the electrode formed by curling of the distal portion has a 2- or 3-dimensional shape in which one or more of the dimensions is larger than the diameter of the lead body.

21. The kit according to claim 1, wherein the lead body has a central portion movable axially within the lead body to move the at least one extendable member between the retracted and extended positions.

22. The kit according to claim 1, in which the extendable member comprises a plurality of extendable members, wherein the distal portions of the extendable members can be selectively deployed such that the electrodes fit a surface of tissue or achieve a desired distribution of current.

23. The kit according to claim 1, wherein the distal tip of the extendable member has a material coating adapted to keep the distal tip straight after deployment past the tip of the lead body, wherein the material will dissolve over time inside the body.

24. The kit of claim 23, wherein the material coating will dissolve by application of electrical current through the distal portion of the extendable members.

25. The kit according to claim 1, wherein the extendable member is small enough to pass through a small body lumen, the distal portion being adapted to be advanced through the small body lumen and to curl into an electrode after being advanced through the small body lumen.

* * * * *